United States Patent
Lauterbach et al.

(10) Patent No.: US 10,245,580 B2
(45) Date of Patent: Apr. 2, 2019

(54) HIGHLY ACTIVE DECOMPOSITION CATALYST FOR LOW CARBON HYDROCARBON PRODUCTION FROM SULFUR CONTAINING FUEL

(75) Inventors: Jochen Lauterbach, Columbia, SC (US); Mary Glascock, Irmo, SC (US); John Bedenbaugh, Columbia, SC (US); Chang-Yin Chien, Columbia, SC (US); Ashok Jangam, Columbia, SC (US); Shahriar Salim, Columbia, SC (US); Sungtak Kim, Columbia, SC (US); Robin Tilburg, Barre, MA (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 13/584,180

(22) Filed: Aug. 13, 2012

(65) Prior Publication Data

US 2013/0041198 A1    Feb. 14, 2013

Related U.S. Application Data

(60) Provisional application No. 61/522,445, filed on Aug. 11, 2011.

(51) Int. Cl.
| | |
|---|---|
| *C07C 4/06* | (2006.01) |
| *C07C 4/02* | (2006.01) |
| *C07C 4/00* | (2006.01) |
| *B01J 29/06* | (2006.01) |
| *C10G 11/05* | (2006.01) |
| *B01J 29/18* | (2006.01) |
| *B01J 29/40* | (2006.01) |
| *B01J 29/44* | (2006.01) |

(52) U.S. Cl.
CPC ............... *B01J 29/06* (2013.01); *C07C 4/06* (2013.01); *C10G 11/05* (2013.01); *B01J 29/18* (2013.01); *B01J 29/405* (2013.01); *B01J 29/44* (2013.01); *C07C 4/00* (2013.01); *C07C 4/02* (2013.01)

(58) Field of Classification Search
CPC .................................... C07C 4/06; C07C 4/02
USPC .................................................. 585/653, 752
See application file for complete search history.

(56) References Cited

U.S. PATENT DOCUMENTS

| | | | | |
|---|---|---|---|---|
| 4,121,996 A | * | 10/1978 | Hilfman | B01J 29/20 208/111.15 |
| 4,437,978 A | * | 3/1984 | Chester et al. | 208/120.05 |
| 5,146,042 A | * | 9/1992 | Gurak et al. | 585/867 |
| 5,316,658 A | * | 5/1994 | Ushio et al. | 208/216 R |
| 5,552,036 A | * | 9/1996 | Foret et al. | 208/236 |

(Continued)

OTHER PUBLICATIONS

Campbell et al., JP-8 catalytic cracking for compact fuel processors, 2004, Journal of Power Sources, vol. 129, pp. 81-89.*

(Continued)

*Primary Examiner* — Youngsul Jeong
(74) *Attorney, Agent, or Firm* — Dority & Manning, P.A.

(57) ABSTRACT

Methods for deriving a low-C hydrocarbon fuel from a high-C hydrocarbon fuel are generally provided. A catalytic material (e.g., an aluminosilicate and/or a zeolite) can be introduced to the high-C hydrocarbon fuel to produce a product stream comprising a low-C hydrocarbon fuel, and the low-C hydrocarbon fuel can be separated in the product stream from any remaining high-C hydrocarbon fuel.

18 Claims, 7 Drawing Sheets

(56) References Cited

U.S. PATENT DOCUMENTS 5,637,207 A * 6/1997 Hsing et al. .................. 208/164
2009/0264693 A1 * 10/2009 Xie et al. ..................... 585/650

OTHER PUBLICATIONS

IS 4576, 1999, Indian Standard Liquefied Petroleum Gases-Specification.*

* cited by examiner

Table 1

| Zeolite (SiO$_2$:Al$_2$O$_3$) | CH$_4$ | C$_2$H$_4$ | C$_2$H$_6$ | C$_3$H$_6$ | C$_3$H$_8$ | C$_4$H$_8$ | C$_4$H$_{10}$ | Total C$_2$-C$_4$ |
|---|---|---|---|---|---|---|---|---|
| MFI (30:1) | 0.7% | 5.1% | 1.2% | 6.2% | 4.4% | 1.6% | 1.7% | 20.2% |
| MFI (50:1) | 0.6% | 5.4% | 1.2% | 7.3% | 3.7% | 2.1% | 1.8% | 21.5% |
| MFI (80:1) | 0.2% | 1.2% | 0.4% | 4.3% | 1.0% | 1.9% | 1.1% | 9.9% |
| MFI (200:1) | 0.1% | 0.5% | 0.2% | 2.6% | 0.5% | 1.3% | 0.7% | 5.7% |
| *BEA (38:1) | 0.2% | 0.2% | 0% | 1.5% | 0.1% | 1.3% | 0.2% | 3.2% |
| MOR (20:1) | 0% | 0% | 0% | 0% | 0% | 0% | 0% | 0% |
| FAU (5.1:1) | 0.8% | 0.6% | 0.2% | 4.5% | 1.4% | 3.0% | 1.0% | 10.8% |
| FAU (80:1) | 0.5% | 0.6% | 0.2% | 4.2% | 1.4% | 2.9% | 0.9% | 10.2% |

Figure 5

Table 2: Typical product distributions for two MFI materials from primary screen at 350°C

| Zeolite | S.A. Ratio (x:1) | Ethylene | Ethane | Propylene | Propane | 1-butene | Butane | Total C2-C4 |
|---|---|---|---|---|---|---|---|---|
| MFI | 23 | 0.40% | 0.00% | 2.20% | 3.95% | 1.95% | 2.70% | 11.20% |
| MFI | 30 | 0.36% | 0.00% | 1.66% | 2.73% | 1.44% | 2.15% | 8.35% |
| MFI | 50 | 0.31% | 0.00% | 1.94% | 2.68% | 1.69% | 2.00% | 8.61% |

Figure 6

Table 3: Catalyst performance after approximately 50 hours on-stream at 350°C

| Zeolite | S.A. Ratio (x:1) | Ethylene | Ethane | Propylene | Propane | 1-butene | Butane | Total C2-C4 |
|---|---|---|---|---|---|---|---|---|
| MFI | 30 | 0.11% | 0.00% | 1.24% | 1.63% | 1.08% | 1.15% | 5.21% |
| MFI | 50 | 0.12% | 0.00% | 1.78% | 1.44% | 1.42% | 1.10% | 5.85% |

Figure 7

| | Ethylene | Ethane | Propylene | Propane | 1-butene | Butane | Total C2-C4 |
|---|---|---|---|---|---|---|---|
| Pt-MFI (50:1) | 0.48% | 0.09% | 3.57% | 0.87% | 2.45% | 0.72% | 8.19% |
| Ga-MFI (50:1) | 0.46% | 0.06% | 2.82% | 0.66% | 1.89% | 0.51% | 6.40% |

Table 4. Conversion Data for a Variety of Ion-exchanged Aluminosilicate Catalysts at 450°C after 50 hours on stream.

HIGHLY ACTIVE DECOMPOSITION CATALYST FOR LOW CARBON HYDROCARBON PRODUCTION FROM SULFUR CONTAINING FUEL

PRIORITY INFORMATION

The present application claims priority to U.S. Provisional Patent Application Ser. No. 61/522,445 titled "Highly Active Decomposition Catalyst for Low Carbon Hydrocarbon Production from Sulfur Containing Fuel" of Lauterbach, et al. filed on Aug. 11, 2011, which is incorporated by reference herein.

GOVERNMENT SUPPORT CLAUSE

This invention was made with government support under W91CRB-10-1-0007 awarded by Defense Advanced Research Projects Agency (DARPA). The government has certain rights in the invention.

BACKGROUND

Aviation fuel (i.e., "jet fuel") generally contains a mixture of high-C hydrocarbons with carbon chains of 8 to 17 carbon atoms per molecule. For example, the high-C hydrocarbons can be a mixture of carbon chains that typically contain between six and 16 carbon atoms per molecule. For example, JP-8 (for "Jet Propellant 8") is a kerosene-based jet fuel, specified in 1990 by the U.S. government as a replacement for government diesel fueled vehicles.

Commercial aviation uses a similar mixture under the name Jet-A, and the U.S. Navy uses a similar formula, under the name JP-5. In addition to powering aircraft and other tactical vehicles, JP-8 is also widely used to power heaters and generate electricity in diesel-type generators. Thus, a strong advantage of JP-8 is its widespread existing supply infrastructure and distribution network. The use of a single fuel greatly simplifies logistics.

However, low-C hydrocarbon fuels (e.g., propane) are often needed by military personnel on the ground and for emerging technologies in remote regions. Low-C hydrocarbon fuels are needed for powering unmanned aerial vehicles, improving the efficiency of auxiliary power systems, and for endothermic fuel applications. If such low-C hydrocarbon fuels could be derived from the high-C hydrocarbon fuel already used by the military, the logistics required for providing a single fuel would be greatly simplified.

JP-8 fuel may contain up to 3,000 ppmw sulfur. As in other higher boiling point hydrocarbon fractions, the sulfur is present largely in the form of thiophene derivatives, including benzothiophenes and dibenzothiophenes. Due to the high sulfur content, most catalyst discovery for JP-8 processing has used synthetic and/or desulfurized fuel.

As such, a need exists for catalytic materials and methods for providing a low-C hydrocarbon decomposition product (e.g., propane) from sulfur containing high-C hydrocarbon fuel (e.g., JP-8).

DEFINITIONS

As used herein, the term "low-C hydrocarbon fuel" refers to a mixture of hydrocarbons having carbon chains that contain 2 to 4 carbon atoms per molecule, such as 2 to 4 carbon atoms per molecule, including but not limited to alkanes (e.g., ethane, propane, butane), alkenes (e.g., ethylene, propylene, butylene), etc. For example, "low-C hydrocarbon fuel" can refer to liquefied petroleum gas, which is mixture primarily of propane and butane, but may also contain small amounts of propylene and/or butylene as well as other low-C hydrocarbons.

Alternatively, the term "high-C hydrocarbon fuel" refers to a mixture of hydrocarbons having carbon chains that contain at least 8 (e.g., 8 to 17) carbon atoms per molecule. For example, "high-C hydrocarbon fuel" can refer to aviation fuel or jet fuel (e.g., JP-8).

SUMMARY

Objects and advantages of the invention will be set forth in part in the following description, or may be obvious from the description, or may be learned through practice of the invention.

Methods are generally provided for deriving a low-C hydrocarbon fuel from a high-C hydrocarbon fuel. In one embodiment, a catalytic material (e.g., an aluminosilicate and/or a zeolite) can be introduced to the high-C hydrocarbon fuel to produce a product stream comprising a low-C hydrocarbon fuel, and the low-C hydrocarbon fuel can be separated in the product stream from any remaining high-C hydrocarbon fuel.

Other features and aspects of the present invention are discussed in greater detail below.

BRIEF DESCRIPTION OF THE FIGURES

A full and enabling disclosure of the present invention, including the best mode thereof to one skilled in the art, is set forth more particularly in the remainder of the specification, which includes reference to the accompanying figures.

FIG. 5 shows a table (Table 1) of typical product distributions for zeolite catalyst materials from primary screen at 550° C.

FIG. 6 shows a table (Table 2) of typical product distributions for two MFI materials from primary screen at 350° C.

FIG. 7 shows a table (Table 3) of catalyst performance after approximately 50 hours on-stream at 350° C.

FIG. 8 shows a table (Table 4) of the conversion data for a variety of ion-exchanged aluminosilicate catalysts at 450° C. after 50 hours on stream.

DETAILED DESCRIPTION

Figure 1:
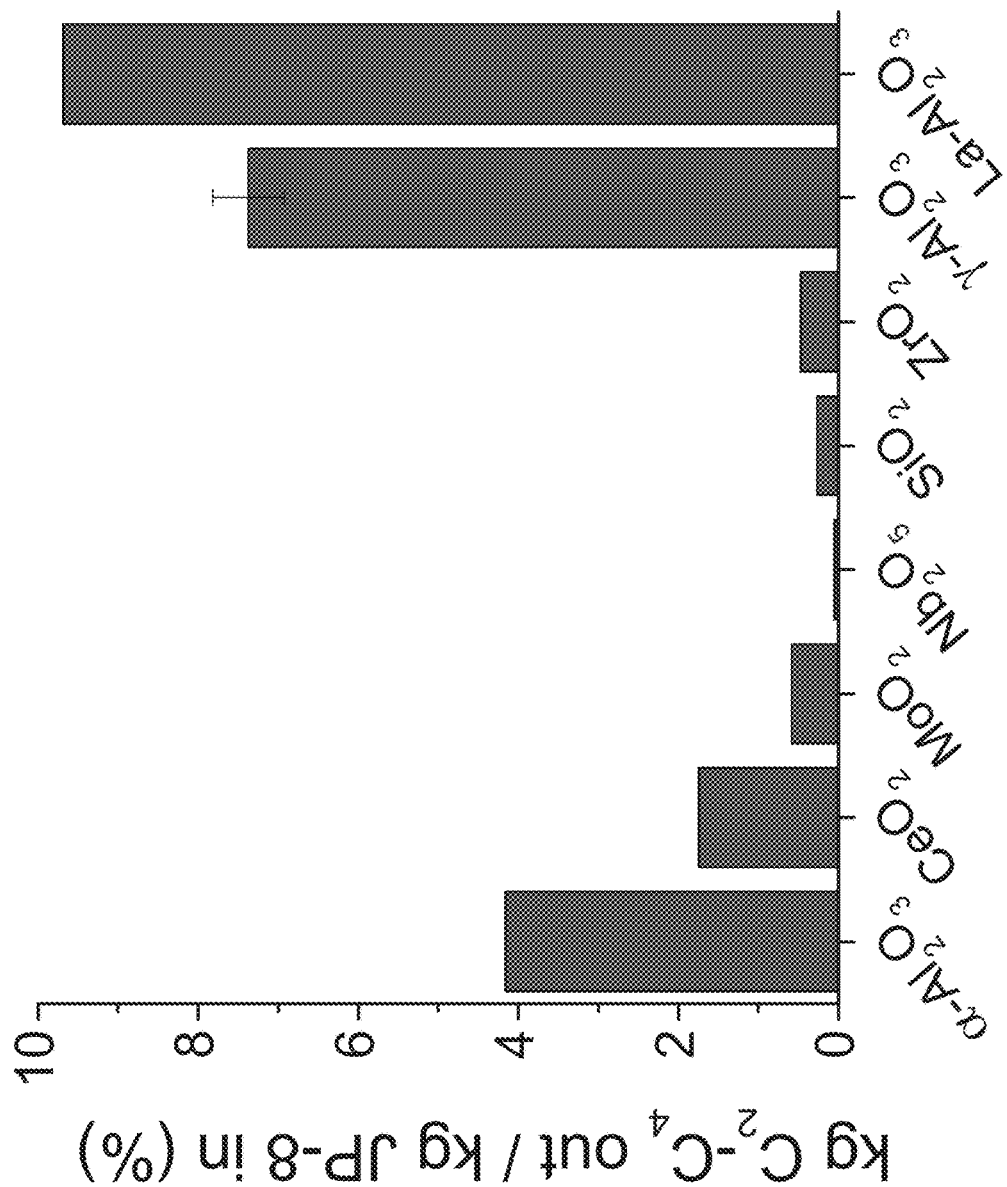
FIG. 1 shows the conversion data for a variety of catalyst support materials.

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

Methods are generally disclosed for deriving a low-C hydrocarbon fuel from a high-C hydrocarbon fuel. According to this method, the low-C hydrocarbon fuel can include hydrocarbons having 2 to 4 carbons per molecule. For example, the low-C hydrocarbon fuel can include a mixture of various concentrations of any or all of the following components: ethylene, ethane, propylene, propane, 1-butene, butane, etc. In one particular embodiment, at least 50% of the low-C hydrocarbon fuel can be hydrocarbons having 3 carbons (e.g., propane).

In contrast to reforming processes, embodiments of the presently disclosed cracking methods involve no reactant inputs in addition to the hydrocarbon fuel for JP-8 processing. Cracking breaks longer-chain, higher molecular weight hydrocarbon molecules into lighter fractions. The cracking mechanism is promoted by solid acid catalysts, such as silica-aluminas and zeolites. As such, methods and catalysts are generally provided for cracking of a high-C hydrocarbon fuel, such as JP-8, into a product mixture of hydrocarbons having carbon chains that contain between 2 and 4 carbon atoms per molecule.

The presently disclosed methods are especially useful for the conversion of sulfur containing, high-C hydrocarbon fuel because the methods do not require desulfurization of the fuel. In particular, the fuel does not need to be desulfurized before reaching the catalyst. That is, the sulfur-containing molecules can be separated from the low-C hydrocarbon fuel, along with any unreacted high-C hydrocarbons, during their production. For example, the sulfur content in the low-C hydrocarbon fuel can be less than 100 ppm, such as less than 50 ppm.

The conversion efficiency of high-C hydrocarbons to low-C hydrocarbons can be up to 25%, calculated on a mass basis (i.e., kg of low-C hydrocarbons out per kg of high-C hydrocarbons (e.g., JP-8) in. However, it is envisioned that higher conversion efficiencies may be realized through optimization of the conversion parameters (e.g., the reactor conditions, etc.).

I. Catalytic Material

The low-C hydrocarbon fuel can be derived from a high-C hydrocarbon fuel through introduction of a catalytic material to the high-C hydrocarbon fuel. Catalysts, according to particular embodiments of the present invention, comprise aluminosilicate materials known as zeolites with mordenite framework inverted (MFI) structure.

Zeolite materials are high surface area supports that have a high activity for many reforming reactions. In one particular embodiment, the zeolite material can be a mixture of alumina and silica having a Si/Al ratio selected to control the total acidity as well as acid site strength. Such zeolites can be prepared by mixing sodium aluminate and sodium silicate, followed by controlled crystallization, usually in the presence of a structure-directing template. Syntheses often must be prepared in hydrothermal conditions at elevated pressure. They can also be easily cation exchanged. Variation of the alumina and silica contents can alter the properties of these materials and tailor their activity for different reactions. Specifically, activity and stability of the catalysts are affected by the silica-to-alumina molar ratio present in the structure. In particular embodiments, the silica to alumina molar ratio can be from 20 to 200.

The catalytic material can also include a relatively small amount of a precious metal or combination of precious metals. Incorporation of various metal atoms into the framework of these materials via an ion-exchange process or impregnation process can yield improved performance. For example, metal atoms doped in this way can include aluminum (Al), cerium (Ce), copper (Cu), europium (Eu), iron (Fe), gallium (Ga), gadolinium (Gd), indium (In), iridium (Ir), lanthanum (La), sodium (Na), neodymium (Nd), nickel (Ni), palladium (Pd), praseodymium (Pr), platinum (Pt), rhodium (Rh), ruthenium (Ru), samarium (Sm), zinc (Zn), zirconium (Zr), or mixtures thereof. The precious metal(s) can be included in the catalytic material in a weight percent of about 0.1% to about 10% of the total weight of the catalytic material (e.g., the weight of the zeolite(s) and the precious metal(s)). For instance, in particular embodiments the precious metal(s) can be included in the catalytic material in a weight percent of about 0.5% to about 5% of the total weight of the catalytic material.

II. Conversion of High-C Hydrocarbon Fuel to Low-C Hydrocarbon Fuel

In one particular embodiment, the high-C hydrocarbon fuel can be introduced into a reactor, along with the catalyst material (e.g., the zeolite and optional metal) and heated to a reaction temperature of between about 300° C. to about 700° C.

The reaction proceeds in a continuous manner with inflow of high-C hydrocarbon fuel and outflow of a product stream containing the low-C hydrocarbon fuel. The reaction occurs near atmospheric pressure (e.g., within about 100 mmHg of 760 mmHg) and can reach steady state in a short amount of time (e.g., less than about 15 minutes).

III. Separation of the Low-C Hydrocarbon Fuel

The low-C hydrocarbon fuel can then be separated from any remaining high-C hydrocarbon fuel and/or the catalytic material in the product stream. For example, the low-C hydrocarbon fuel can be separated from any remaining high-C hydrocarbon fuel and/or catalytic material using a condensation process. In one embodiment of a condensation process, the product stream (i.e., the low-C hydrocarbon fuel) from the reactor is cooled to a condensation temperature where any remaining high-C hydrocarbon fuel liquefies. The low-C hydrocarbon fuel remains gaseous and passes through a condenser to remove any unreacted high-C hydrocarbon fuel as liquid waste. For example, the condensation temperature can be about 0° C. to about 10° C. (e.g., less than about 8° C.). At these conditions, the low-C hydrocarbon fuel remains in the gas state and can be separated as the desired product.

EXAMPLES

FIG. 1 shows the activity for a variety of catalyst supports without any impregnated metal toward the JP-8 cracking reaction. The metric used to compare catalyst activity between different samples is the weight percent of low-C hydrocarbon fuel in the product stream normalized to the total amount of high-C hydrocarbons fed into the reactor. By this metric, alumina based support materials showed activity for JP-8 cracking above the 5% minimum target for JP-8 conversion; however, the temperatures to reach such conversions were 650° C. and above. Based on these data, alumina supports were doped with rare earth metals (e.g., La) and tested, which led to a top performance close to 10% conversion of JP-8 to low-C hydrocarbons at 650° C. Although this formulation met the requirements of above 5% conversion, the catalyst operating temperature of 650° C. is very high and would require a substantial energy input for reactor heating during operation and might lead to fairly rapid degradation of the catalytic material.

Figure 2:
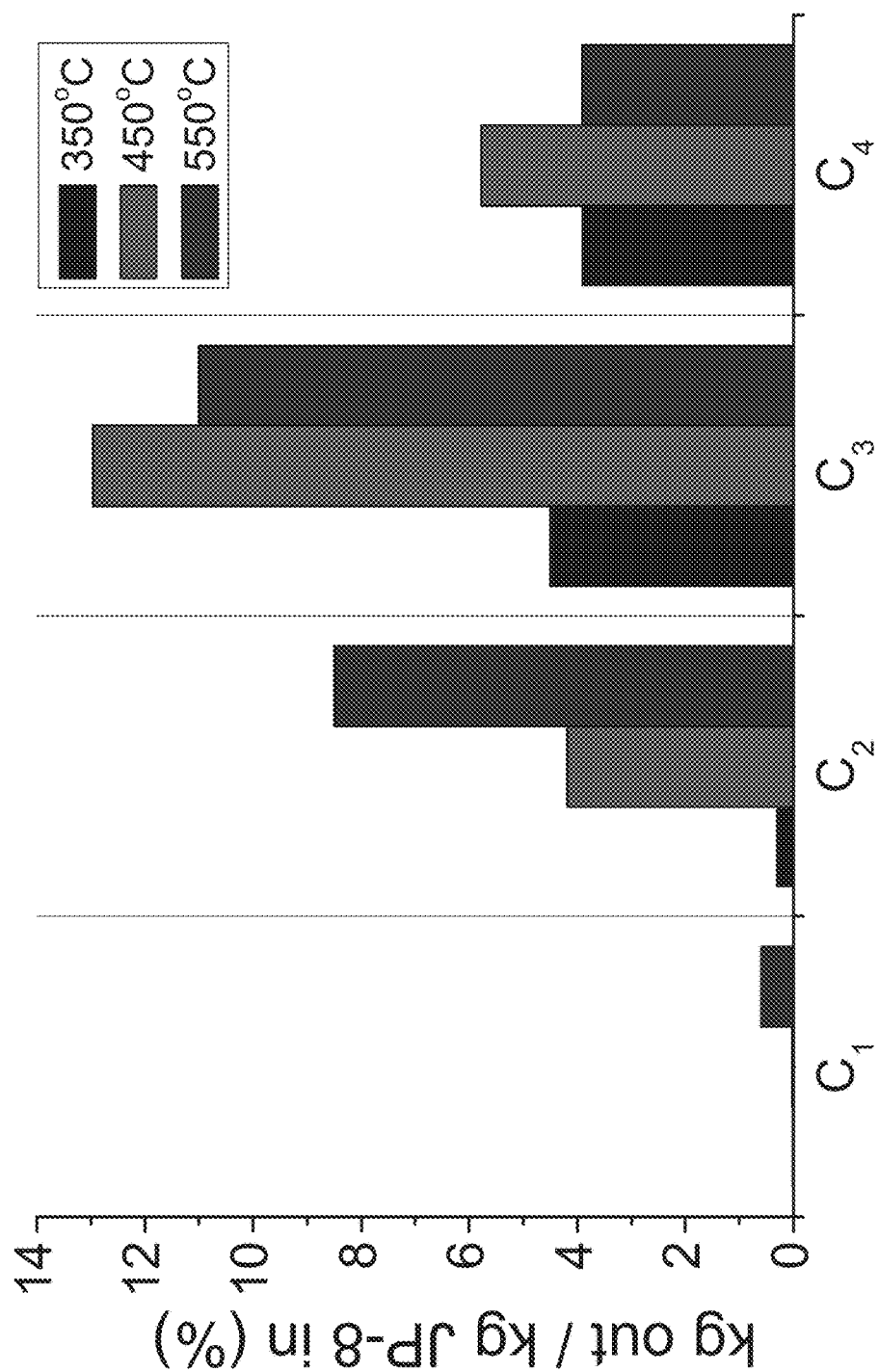
FIG. 2 shows the primary screen conversion data for different materials at 350° C. (left column), at 450° C. (middle column), and at 550° C. (right column).

Primary screen conversion data for a variety of aluminosilicate catalysts were obtained. Despite possible sensitivity to sulfur poisoning, the results showed that initial JP-8 conversions to the desired products of over 20% were observed with longer term conversions above 10% after 10 hours of time on stream. Table 1 shows the selective yields (mass %) of JP-8 cracking to $C_1$-$C_4$ hydrocarbons over zeolite catalysts with various $SiO_2$:$Al_2O_3$ ratios at a reactor temperature of 550° C. The best observed conversion of JP-8 to low-C hydrocarbon fuel is above 20% for the best MFI catalysts. FIG. 2 shows the initial JP-8 conversion product distribution to products containing 2, 3, or 4 carbon atoms, a high activity MFI catalyst. Even at 350° C., the best observed initial conversion is well above 10%, as shown in Table 2. Table 3 demonstrates catalyst performance after approximately 50 hours on stream. During this time, several start-up/shut-down cycles were also simulated, where the gas feed was cut and the catalysts were cooled to room temperature, left there for several hours and then heated up again.

The results clearly show that zeolites are superior materials as compared to metals on oxide supports for the targeted reaction. Particularly surprising was the long-term activity, where after 50 hours on stream, as shown in Table 3, almost 6% conversion of JP-8 to low-C hydrocarbons was obtained at a relatively low reaction temperature of 350° C. The Si/Al ratio of the samples influences the overall conversion behavior and the specific product distribution, which provides a unique opportunity for further optimization. Deactivation studies of the catalyst materials that were performed in parallel, using a combination of electron microscopy, X-ray diffraction, and elemental analysis, have shown that coking is the major deactivation mechanism. In very few instances could any traces of sulfur could be found on deactivated samples. Catalyst activity could be regenerated using coke burnoff processes.

Metal modifiers can be loaded onto the zeolite catalysts via ion exchange or impregnation to give unique catalytic properties and enhance catalyst activity. Ion-exchanged zeolites were screened for long term activity while substituting various metals into the lattice structure.

Zeolites can be ion exchanged to give unique catalytic properties. Additional equipment was procured for synthesizing ion-exchanged zeolites with tunable properties to enhance catalyst activity. A first batch of ion-exchanged zeolites has been synthesized and has been screened for long term activity while substituting various metals into the lattice structure. Table 4 compares the conversion for two ion-exchanged zeolites. Ion exchange so far was performed with Fe, Cu, Ga, Pt, Ni, and Gd. Although some samples showed high initial activity, only the Pt and Ga ion exchanged zeolites showed long-term sustained activity above the 5% conversion target. These results show that further substantial improvements in long-term activity can be achieved through ion-exchange of these materials.

Figure 3:
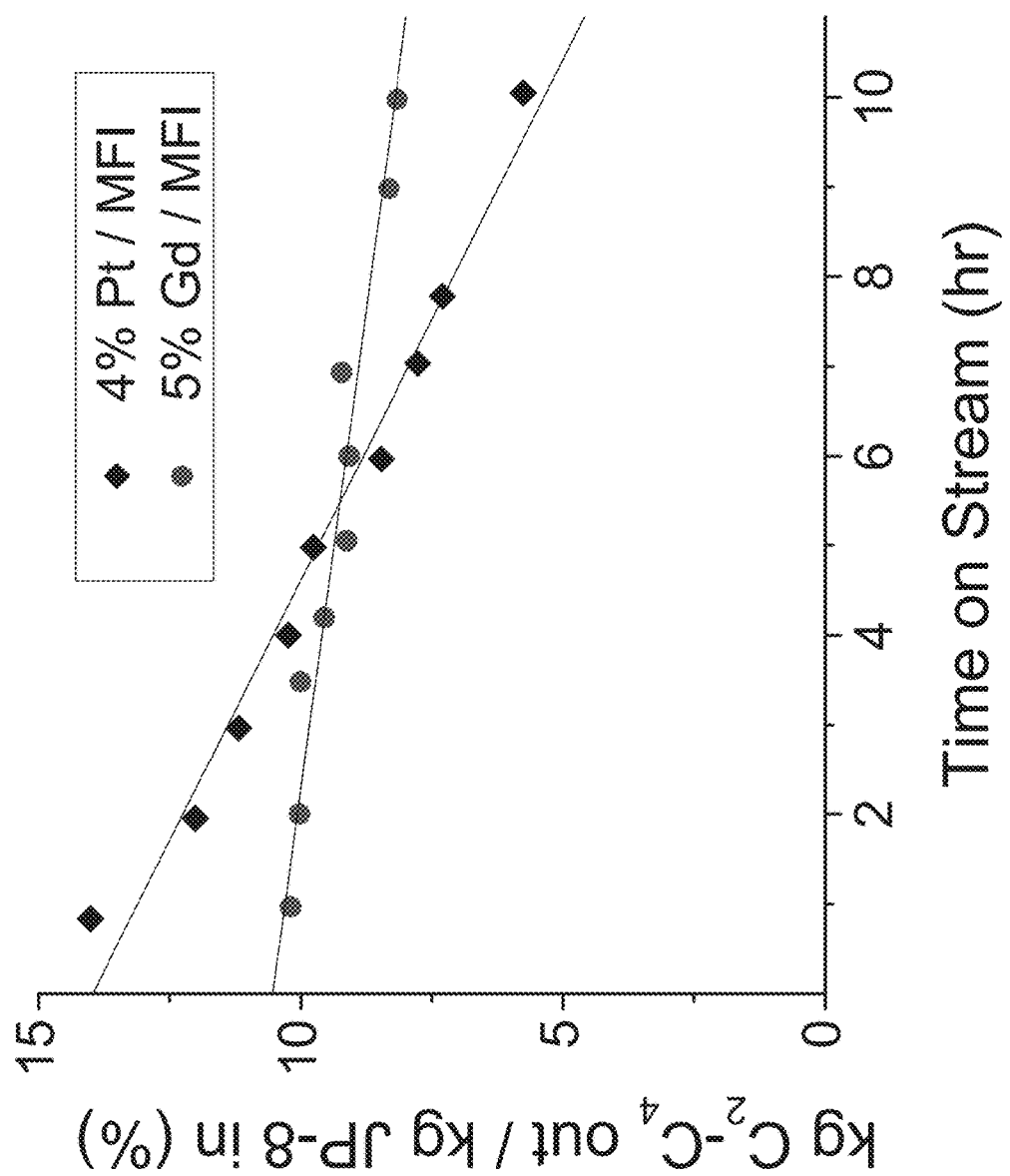
FIG. 3 shows a comparison of the time on stream JP-8 conversion to low-C hydrocarbon fuel for two metal-loaded MFI catalysts at a reactor temperature of 450° C.
Figure 4:
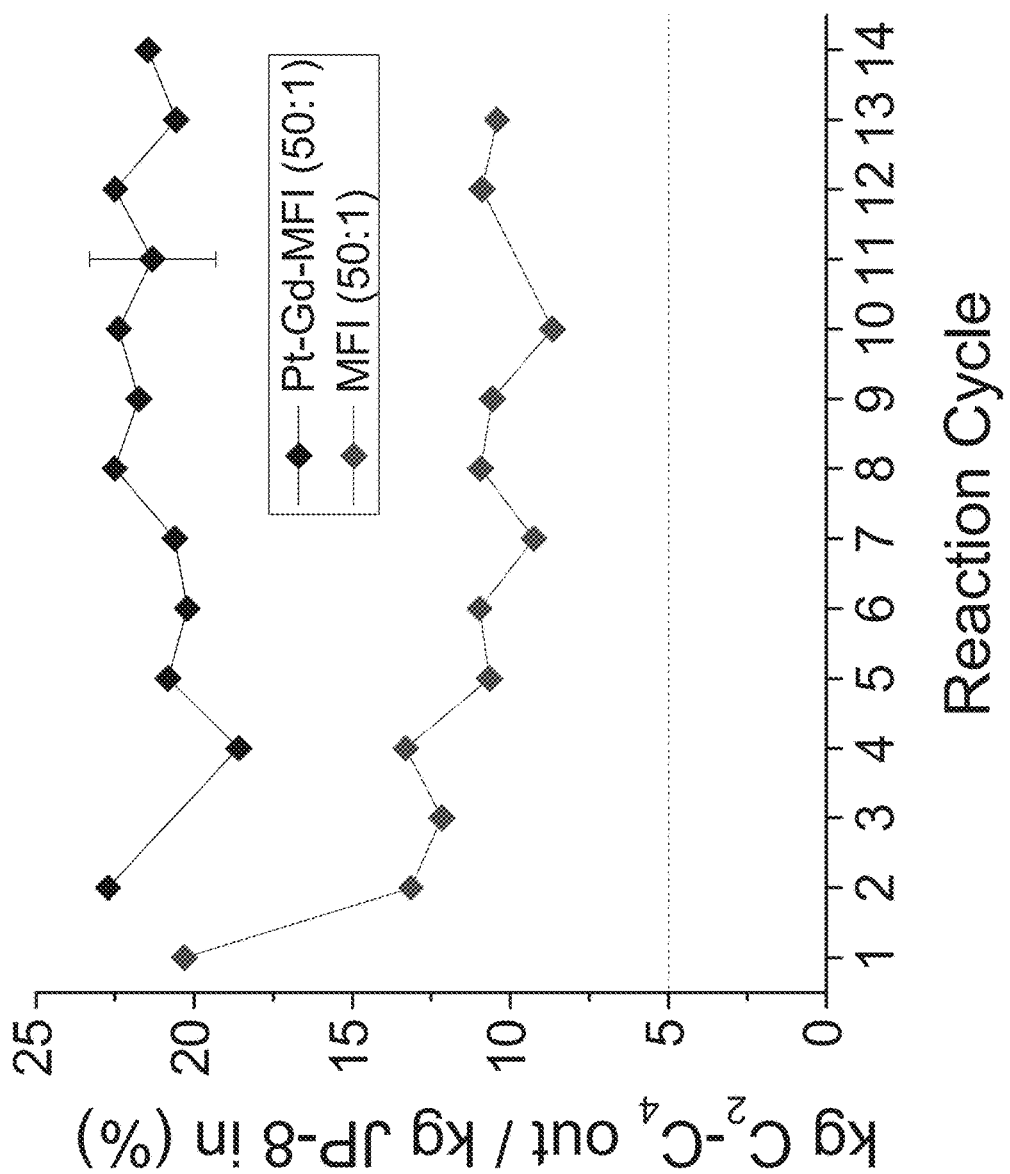
FIG. 4 shows a comparison of the JP-8 conversion to low-C hydrocarbon fuel for a MFI catalyst loaded with Pt (top line) and Gd (bottom line) as compared to the base catalyst. Conversion was measured following each 1 hour coke burnoff regeneration interspersed with repeated 5 hour reaction cycles at a reactor temperature of 450° C.

FIG. 3 shows a comparison of the time on stream conversion of JP-8 to low-C hydrocarbons for a MFI catalyst loaded with 4% Pt and 5% Gd. The Pt-loaded catalyst has higher initial activity, while the Gd-loaded catalyst exhibits a slower rate of deactivation. In addition, the Pt-loaded catalyst facilitates coke burnoff regeneration at lower temperatures. A MFI catalyst containing a combination of Pt and Gd metal loadings was found to produce low-C hydrocarbon yields from a high-C fuel of approximately 20% on a mass basis through repeated reaction and regeneration cycles at a moderate reactor temperature of 450° C. This catalyst successfully achieved this performance without degradation in activity, as shown in FIG. 4.

These and other modifications and variations to the present invention may be practiced by those of ordinary skill in the art, without departing from the spirit and scope of the present invention, which is more particularly set forth in the appended claims. In addition, it should be understood that the aspects of the various embodiments may be interchanged both in whole or in part. Furthermore, those of ordinary skill in the art will appreciate that the foregoing description is by way of example only, and is not intended to limit the invention so further described in the appended claims.

What is claimed:

1. A method for deriving a low-C hydrocarbon fuel from a sulfur containing, high-C hydrocarbon fuel, the method comprising:
   introducing a catalytic material to the sulfur containing, high-C hydrocarbon fuel, upon which a reaction occurs, to produce a product stream comprising a low-C hydrocarbon fuel, wherein the catalytic material comprises a zeolite comprising ion exchanged Pt, wherein the ion exchanged Pt is included in the catalytic material in a weight percent of about 0.1% to about 10% of the total weight of the catalytic material, and wherein the sulfur containing, high-C hydrocarbon fuel comprises about 200 ppm to about 3000 ppm sulfur; and
   separating the low-C hydrocarbon fuel in the product stream from any remaining sulfur containing, high-C hydrocarbon fuel, and wherein the low-C hydrocarbon fuel has a sulfur content that is less than 100 ppm, wherein the low-C hydrocarbon fuel is separated from any remaining sulfur containing, high-C hydrocarbon fuel in the product stream through a condensation process.

2. The method as in claim 1, further comprising:
   heating the catalytic material and the sulfur containing, high-C hydrocarbon fuel to a reaction temperature of between about 300° C. and about 700° C. to produce the product stream.

3. The method as in claim 1, wherein the low-C hydrocarbon fuel is produced from the sulfur containing, high-C hydrocarbon fuel in a reactor that includes the catalytic material.

4. The method as in claim 3, wherein the sulfur containing, high-C hydrocarbon fuel is introduced into the reactor as a continuous inflow stream.

5. The method as in claim 3, wherein a continuous outflow of the product stream exits the reactor.

6. The method as in claim 1, wherein the condensation process comprises:
   cooling the product stream to a condensation temperature where any remaining sulfur containing, high-C hydrocarbon fuel liquefies while the low-C hydrocarbon fuel remains gaseous; and
   collecting the low-C hydrocarbon fuel.

7. The method as in claim 6, wherein the condensation temperature is about 0° C. to about 10° C.

8. The method as in claim 1, wherein the catalytic material comprises an aluminosilicate material with mordenite framework inverted structure.

9. The method as in claim 1, wherein the catalytic material comprises an aluminosilicate material having silica to alumina molar ratio of from 20 to 200.

10. The method as in claim 1, wherein the catalytic material further comprises a metal selected from the group consisting of Al, Ce, Cu, Eu, Fe, Gd, In, Ir, La, Na, Nd, Ni, Pd, Pr, Rh, Ru, Sm, Zn, Zr, and mixtures thereof.

11. The method as in claim 10, wherein the metal is included in the catalytic material in a weight percent of about 0.1% to about 10% of the total weight of the catalytic material.

12. The method as in claim 10, wherein the metal is included in the catalytic material in a weight percent of about 0.5% to about 5% of the total weight of the catalytic material.

13. The method as in claim 1, wherein the reaction occurs at a reaction pressure of from about 100 mmHg to 760 mmHg.

14. The method as in claim 1, wherein the reaction occurs at atmospheric pressure.

15. The method as in claim 1, wherein any sulfur-containing molecules are separated from the low-C hydrocarbon fuel in the product stream.

16. The method as in claim 1, wherein the low-C hydrocarbon fuel has a sulfur content that is less than 50 ppm.

17. The method as in claim 1, wherein the zeolite further comprises Gd.

18. The method as in claim 1, wherein the ion exchanged Pt is included in the catalytic material in weight percent of about 0.5% to about 5% of the total weight of the catalytic material.

* * * * *